(12) United States Patent
Zavrel et al.

(10) Patent No.: US 10,876,141 B2
(45) Date of Patent: Dec. 29, 2020

(54) PROCESS FOR THE HYDROLYSIS OF BIOMASS

(71) Applicant: CLARIANT INTERNATIONAL LTD., Muttenz (CH)

(72) Inventors: Michael Zavrel, Olching (DE); Markus Zehe, Munich (DE); Joerg Bartuch, Gauting (DE); Marcus Verhuelsdonk, Germering (DE)

(73) Assignee: Clariant International Ltd., Muttenz (CH)

( * ) Notice: Subject to any disclaimer, the term of this patent is extended or adjusted under 35 U.S.C. 154(b) by 377 days.

(21) Appl. No.: 15/567,765

(22) PCT Filed: May 12, 2016

(86) PCT No.: PCT/EP2016/060747
§ 371 (c)(1),
(2) Date: Oct. 19, 2017

(87) PCT Pub. No.: WO2016/192955
PCT Pub. Date: Dec. 8, 2016

(65) Prior Publication Data
US 2018/0119189 A1    May 3, 2018

(30) Foreign Application Priority Data
May 29, 2015   (EP) ................................... 15169886

(51) Int. Cl.
| | | |
|---|---|---|
| *C12P 19/14* | (2006.01) | |
| *C12P 7/06* | (2006.01) | |
| *C12P 7/08* | (2006.01) | |
| *C12P 7/10* | (2006.01) | |
| *C13K 1/02* | (2006.01) | |

(52) U.S. Cl.
CPC .................. *C12P 19/14* (2013.01); *C12P 7/06* (2013.01); *C12P 7/08* (2013.01); *C12P 7/10* (2013.01); *C12Y 302/01004* (2013.01); *C13K 1/02* (2013.01); *Y02E 50/10* (2013.01)

(58) Field of Classification Search
CPC .... C12P 19/14; C12P 7/06; C12P 7/10; C12P 7/08; C13K 1/02; C12Y 302/01004; C11D 3/38636
See application file for complete search history.

(56) References Cited

U.S. PATENT DOCUMENTS

| | | | |
|---|---|---|---|
| 2009/0035826 A1* | 2/2009 | Tolan | B01D 3/001 435/99 |
| 2014/0187825 A1* | 7/2014 | Binder | C12P 7/14 568/840 |

FOREIGN PATENT DOCUMENTS

| | | |
|---|---|---|
| CN | 101186943 A | 5/2008 |
| EP | 1130085 A1 | 9/2001 |
| EP | 2256208 A1 | 12/2010 |
| EP | 2548965 A1 | 1/2013 |
| WO | 2003093420 A2 | 11/2003 |
| WO | 2009061740 A2 | 5/2009 |
| WO | WO 2013062407   * | 5/2013 |
| WO | 2014075694 A1 | 5/2014 |
| WO | 2014100685 A1 | 6/2014 |
| WO | 2014144565 A1 | 9/2014 |

OTHER PUBLICATIONS

Bradford, Marion M.; A Rapid and Sensitive Method for the Quantitation of Microgram Quantities of Protein Utilizing the Principle of Protein-Dye Binding; Analytical Biochemistry, 1976, pp. 248-254, vol. 72.
Yang, Bin et al., "Enzymatic hydrolysis of cellulosic biomass", Biofuels (2011) 2(4), 421-450.

* cited by examiner

*Primary Examiner* — Thane Underdahl
(74) *Attorney, Agent, or Firm* — Verrill Dana, LLP

(57) ABSTRACT

The present invention is directed to a novel and advantageous process for the hydrolysis of biomass which enables a thorough hydrolyzation also of recalcitrant biomass such as sugar cane straw and sugar cane bagasse.

9 Claims, 3 Drawing Sheets

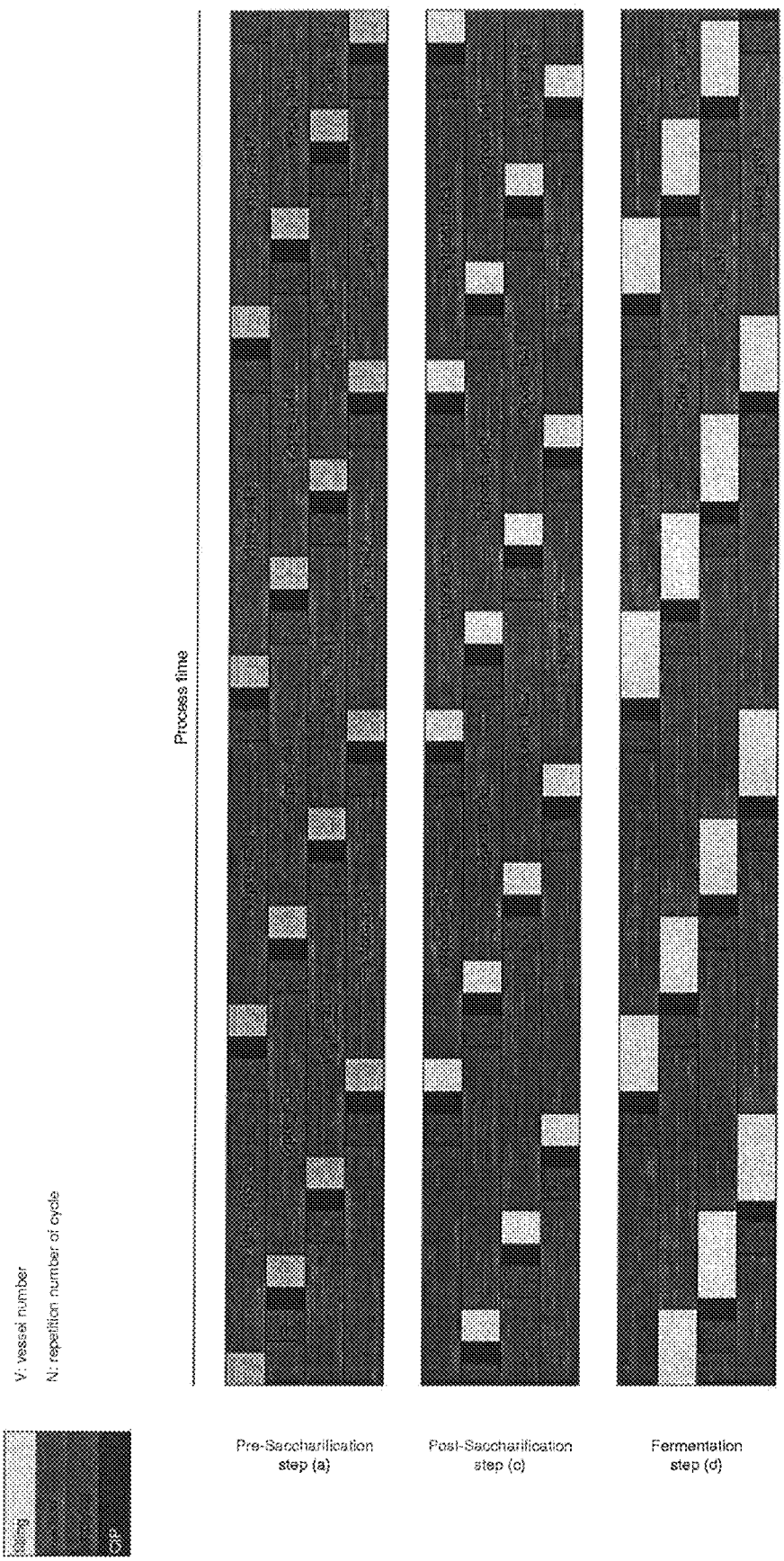

PROCESS FOR THE HYDROLYSIS OF BIOMASS

CROSS REFERENCE TO RELATED APPLICATIONS

This application claims the priority of PCT/EP2016/060747, filed on 12 May 2016, which claims priority to European Patent Application No. 15169886.7, filed on 29 May 2015, the entire contents of each of which are hereby incorporated in total by reference.

The present invention is directed to a novel and advantageous process for the hydrolysis of biomass which enables a thorough hydrolyzation also of recalcitrant biomass such as sugar cane straw and sugar cane bagasse.

Biomass originating from crops such as sugar beet, sugar cane, corn, straw and other saccharide- or polysaccharide- and protein-containing material are valuable sources not only for refined saccharides such as monomeric or dimeric sugars, but also for other components such as amino acids, proteins and minerals.

There are processes within the state of the art for hydrolyzing and separating and refining single components such as sugars from sugar beets and sugar cane. In such processes, however, other valuable components such as cell wall compounds and proteins are discarded after extraction and refining of monomeric and dimeric sugars such as sucrose. Within a well established process sugar is removed from e.g. sugar beet or sugar cane by extracting sliced sugar beet or cane with hot water in a continuous counter-flow process. Usually, such processes require the addition of further agents such as CaO in an amount of around 1 to 3 kg of CaO per 100 kg of biomass. Products of this process are the sugar solution, called raw juice, and the so-called beet pulp or sugar-cane bagasse. The raw juice is further purified and filtrated, and subsequently concentrated to yield thick juice (65 to 70% dry matter content), or, after crystallization, to yield refined sugar. The elevated temperature and pH conditions during this process cause the destruction of a crucial amount of monosaccharides contained in the solution. Further, due to the decomposition of nitrogen compounds ammonia is produced. In addition, the so called beet-pulp or sugar-cane bagasse still contains not only the majority of proteins of the sugar beet or cane but also the majority of polysaccharides such as cellulose, hemicellulose and pectin.

A favorable process which uses enzymes for beet-pulp hydrolysis is described in EP 2 256 208 A1, however, the resulting product still contains solid-components of the sugar beet.

Due to their recalcitrance the industry faces even greater obstacles when sugar cane straw or sugar cane bagasse is used as source material for obtaining mono- and dimeric sugars and other valuable components. This recalcitrance is caused by a low accessibility of cellulose due to the embedding of the cellulose fibers into lignin and other polymeric substances. Within the processes known within the state of the art liquefaction is rarely exceeding 60 wt-% of the initial biomass material.

Thus, there is a need for an improved process for the hydrolysis of biomass in that not only a high amount of monomeric and dimeric sugars may be obtained but also the impact of inhibition of hydrolysis and/or subsequent fermentation processes due to formation of compounds inhibitory to hydrolyzing enzymes and/or microorganisms might be minimized. Further, there is a need for an energy-efficient and economical process.

It is thus the object underlying the present invention to provide a process for hydrolyzing biomass which does not show any of the disadvantages of the processes known within the state of the art.

In a first aspect, the invention thus provides a process for hydrolyzing biomass comprising the steps of
a) Contacting the biomass with an enzyme-composition containing at least one enzyme selected from the class of hydrolases in a vessel;
b) Separating a solid and a liquid phase;
c) Enzymatic conversion of the solid phase;
d) Combining at least part of the converted solid phase of step (c) with the liquid phase of step (b).

The term "biomass" as used within the present invention refers to any type of biomass known to a person skilled in the art as suitable for the inventive process. Particularly preferred is biomass of plant-origin. Within a further preferred embodiment, the initial dry matter content of the biomass is selected from 10 to 100 wt.-%, more preferred from 35 to 95 wt.-% and particularly preferred from 40 to 80 wt.-%. The term "dry matter" (d.m.) refers to the mass to biomass ratio determined after water and other volatile compounds have been removed from fresh tissue using an IR-balance. It is thereby particularly preferred to select a biomass whereby its dry matter contains at least 25 wt.-% of saccharides such as monomeric sugars, dimeric sugars and oligosaccharides and/or polysaccharides, more preferred at least 40 wt.-%, particularly preferred at least 60 wt.-%, further preferred at least 80 wt.-% of saccharides such as monomeric sugars, dimeric sugars and oligosaccharides and/or polysaccharides. Further, any mixtures of suitable biomasses are to be included within the term "biomass".

Particularly preferred biomass is selected from "sugar beet biomass" and/or "sugar cane biomass" and/or "lignocellulose biomass". The term "sugar beet biomass" refers to the complete and unprocessed root tissue of *Beta vulgaris* including the outer peel and the internal pulp. Dry tissue of *Beta vulgaris* contains 80% wt.-% soluble sucrose, while beet pulp contains approximately 7% pectin, 7% cellulose and 7% hemicellulose, 17% arabinose, 20% glucose and 3.5% fructose and 10% proteins, all relative to the dry matter (d.m.) of the biomass. The term "sugar beet biomass" further comprises sugar beet pulp (sugar beet chips).

The term "sugar cane biomass" refers to the complete and unprocessed stalks of *Saccharum* sp. including the outer peel and the internal pulp. Dry tissue of *Saccharum* sp. contains 80% wt.-% soluble sucrose, while dry cane bagasse is made up of approximately 70% polymeric sugars, including 45% cellulose, 23% lignin and 25% hemicellulose primarily in the form of xylan all relative to the dry matter (d.m.) of the biomass. The term "sugar cane biomass" further comprises sugar cane pressed cake (bagasse). Particularly preferred are sugar cane bagasse and sugar cane straw.

The term "lignocellulose biomass" refers to residue-, waste- and/or by-products from forestry and agriculture, the food-processing and paper industry and communal waste. In particular, the term "lignocellulose biomass" as used within the present invention includes grain straw and/or spelt (such as wheat, rye, barley, oats), maize straw, stover and/or spindles, grasses such as *Sericea lespedeza*, switchgrass (*Panicum virgatum*), Napier grass (*Miscanthus*; China reed), Sudan grass (*Sorghum sudananse, Sorghum drummondi*), Arundo donax, barks, wood, wood residues, wood chips and/or wood chippings, fruit pulp, rice straw, banana leaves, empty fruit bunches and agave residues.

Further biomass suitable for the process are manure from stables, herbaceous materials, coffee grinds and waste from oil mills such as rapeseed pressed cake and sewage from mills, paper-making stock and waste water from paper mills, waste paper, vegetable and fruit leftovers.

Within a preferred embodiment of the process of the present invention, the biomass is selected from cellulose, hemicellulose and/or lignin-containing biomass.

Within a particularly preferred embodiment of the process of the present invention the biomass is selected from sugar beet, sugar beet pulp, sugar cane, sugar cane bagasse, sugar cane straw, wheat straw, corn, wood, oilseed and mixtures thereof.

Within another particularly preferred embodiment of the process of the present invention the biomass is lignocellulosic biomass from agricultural residues, such as wheat straw, sugar cane bagasse, sugar cane leaves and stalks, sugar cane straw, maize straw, stover and mixtures thereof.

The term "hydrolysis" as used within the present invention is to be understood as depolymerization of a polymer by a hydrolysis reaction. Hydrolysis reaction is to be understood as the cleavage of chemical bonds by the addition of water. One way to perform hydrolysis technically is to add hydrolase enzymes to the biomass.

Preferably due to the process for the hydrolysis of biomass according to the present invention, saccharides are obtained from the biomass material, wherein it is particularly preferred that at least 50 wt.-% of the saccharides obtained are in the form of monomeric and dimeric sugars, preferably at least 65 wt.-%, more preferred at least 75 wt.-%, also preferred at least 85 wt.-% and most preferred 99 wt.-% all relative to the dry matter (d.m.) of the biomass. It is further possible to obtain amino acids, oligopeptides, oligosaccharides and/or proteins from the biomass material when applying the process for the hydrolysis of biomass according to the present invention.

The biomass is preferably washed prior to subjecting it to the enzymatic treatment, and washing water is removed prior to further processing. Moreover, it is preferred to provide the biomass in particulate form e.g. by cutting, milling, grinding, shearing, shear-dispersing, chopping, dispersing and/or blending the biomass prior to step (a). Within a further embodiment, the biomass might be subjected a pre-treatment process before step (a) of the inventive process.

Methods suitable for the pretreatment of the biomass include any kind of mechanical, biological, chemical and/or physical pretreatment methods known to a person skilled in the art. Within a preferred embodiment, the pretreatment method is selected from the methods of mechanical comminution, treatment with acids and/or alkalines, wet oxidation, pH-controlled hydrothermolysis and/or steam explosion.

"Steam explosion" according to the present invention preferably comprises a pressurized hydrothermal treatment at a temperature of from 60 to 350° C., preferably from 80 to 300° C., particularly preferred from 100 to 250° C. and most preferred from 110 to 220° C. of the lignocellulose-containing material in the absence or presence of acid (such as $H_2SO_4$, HCl, $H_3PO_4$) or base/alkaline (i.e. $NH_4OH$, NaOH, KOH, lime) catalysts, which are—if present—added at concentrations from 0.01 to 15% (wt./wt.), preferably from 0.05 to 12.5% (wt./wt.), more preferred from 0.1 to 10% (wt./wt.) and most preferred from 0.25 to 7.5%. In a preferred embodiment of the present invention the pressure is preferably selected from 1 to 100 bar, preferably from 2 to 50 bar, also preferred from 3 to 25 bar and most preferred from 5 to 15 bar. Reaction times during steam explosion have to be selected from 10 s to 2 h, preferably from 1 minute to 1.5 hours, and most preferred from 5 minutes to 1 hour to provide for efficient transformation of the biomass components in preparation for enzymatic hydrolysis. Within a particularly preferred embodiment a "mechanical comminution" pretreatment of the lignocellulose-containing material is carried out before or during the steam explosion pretreatment, wherein the mechanical comminution is selected from the group consisting of mechanical processing, grinding, chopping, crushing, cutting, irradiation, milling and combinations thereof.

"Acid pretreatment" according to the present invention preferably constitutes a continuous dilute and/or mild acid treatment, such as, treatment with sulfuric acid, or another organic acids, such as acetic acid, citric acid, tartaric acid, succinic acid, hydrogen chloride or mixtures thereof. Other acids may also be used. A "mild acid treatment" according to the present invention is to be understood as carried out at a pH of from 0.1 to 5, preferably pH from 2 to 3 (respective to the lignocellulose-containing material). In a preferred embodiment the acid is added in concentrations from 0.01 to 15 wt.-% (wt./wt.), preferably from 0.05 to 12.5 wt.-% (wt./wt.), more preferred from 0.1 to 10 wt.-% (wt./wt.) and most preferred from 0.25 to 7.5 wt.-%.

The acid is preferably sulfuric acid. The acid may be contacted with the biomass at a temperature in the range of from 120 to 280° C., preferably from 135 to 225° C. and most preferred from 150 to 200° C. for a period from 1 to 60 minutes, preferably 2 to 30 minutes and most preferred from 5 to 15 minutes. Addition of strong acids, such as sulphuric acid, may be applied within particularly preferred embodiments to remove hemicellulose.

"Chemical pretreatment" according to the present invention also pertains to treatment of the biomass with $H_2O_2$, ozone, Lewis acids, $FeCl_3$, $Al_2(SO_4)_3$ in aqueous alcohols, glycerol, dioxane, phenol, ethylene glycol, NaOH, $Na_2CO_3$ and/or ammonia. Preferred concentrations, temperature and duration are chosen analogous to the conditions referenced above regarding acid pretreatment.

"Wet oxidation pretreatment" according to the present invention involves the use of oxidizing agents, such as sulphite based oxidizing agents.

The term "mechanical comminution" refers to any mechanical treatment which promotes the separation and/or release of cellulose, hemicellulose and/or lignin from the biomass.

Mechanical comminution is preferably selected from the group consisting of mechanical processing, grinding, chopping, crushing, cutting, irradiation, milling such as dry milling, wet milling and vibratory ball milling, and combinations thereof.

"Biological pretreatment" according to the present invention refers to any biological pretreatment which promotes the separation and/or release of cellulose, hemicellulose, and/or lignin from the biomass. Biological pretreatment techniques can involve applying lignin-solubilizing microorganisms such as actinomycetes (e.g. *Streptomyces* strains) or white rod fungi.

Pretreatment methods suitable for the process of the present invention are to be carried out within suitable devices known to a person skilled in the art. A device suitable for carrying out chemical pretreatment may be any kind of vessel such as a batch reactor. A device suitable for carrying out steam explosion may be any kind of vessel such as a batch reactor but may also be carried out within a screw reactor, preferably a continuous screw reactor.

It is thereby particularly preferred that the pretreatment method is selected from methods not involving the addition of any acid and/or alkalines as the use of these substances will lead to the formation of compounds inhibitory to enzymes and/or microorganisms used during hydrolysis and/or fermentation.

The dry matter content of pretreated biomass is preferably selected from 20 to 60 wt.-%, particularly preferred from 35 to 50 wt.-%, wherein it is most preferred that the biomass has been pretreated by a method not involving the addition of any acid and/or alkalines.

It is, however, a particular advantage of the process for the hydrolysis of biomass that also the application of relatively large and/or un-pretreated biomass particles will still achieve favorable results. The size of the biomass particles is preferably such that at least 90 wt.-% of the particles have a maximum length of 200 mm, more preferred 100 mm, even more preferred 50 mm and most preferred 25. It is further preferred that the size of the biomass particles is preferably such that at least 95 wt.-% of the particles have a maximum length of 200 mm, more preferred of 100 mm, even more preferred of 50 mm and most preferred of 25 mm.

Within step a) of the process for the hydrolysis of biomass, the biomass is contacted with an enzyme-composition containing at least one enzyme selected from the class of hydrolases.

The term "contacting" as used within the process for the hydrolysis of biomass comprises any kind of contacting of biomass with an enzyme composition known to a person skilled in the art as suitable for the inventive process. Within a preferred embodiment, the "contacting" of the biomass with the enzyme composition is carried out by adding the enzyme composition to the biomass. Further, it is particularly preferred that the addition of the enzyme composition is followed by or carried out concurrently with a mixing of the enzyme composition and the biomass.

The term "enzyme composition" as used within the present invention of the process for the hydrolysis of biomass refers to any composition comprising at least one enzyme selected from the class of hydrolases. The at least one enzyme selected from the class of hydrolases amounts preferably to from 1 to 99.99 wt.-% (relative to the weight of the enzyme composition), further preferred to from 5 to 99 wt.-%, particularly preferred to from 10 to 95 wt.-% and most preferred to from 20 to 90 wt.-% and may further contain at least one enzyme selected from the class of lyases. Within embodiments of the present invention, wherein the enzyme-composition contains at least one enzyme selected from the class of lyases, the at least one enzyme selected from the class of hydrolases preferably amounts to from 0.01 to 50 wt.-% (relative to the weight of the enzyme composition), preferred to from 0.05 to 20 wt.-%, more preferred to from 0.08 to 5 wt.-% and most preferred to from 0.1 to 1 wt.-%.

Within a preferred embodiment of the process of the present invention for the hydrolysis of biomass, the enzyme composition contains cellulases, hemicellulases and/or pectinases.

Within a particularly preferred embodiment of the process for the hydrolysis of biomass the enzyme composition contains at least one cellobiohydrolase (EC 3.2.1.-) and at least one endo-,4-β-glucanase (EC 3.2.1.4).).

Within a particularly preferred embodiment of the process for the hydrolysis of biomass the enzyme composition contains at least one cellobiohydrolase (EC 3.2.1.-), at least one endo-,4-β-glucanase (EC 3.2.1.4).), at least one ß-glucosidase (EC 3.2.1.4), at least one glycoside hydrolase 61 (GH61 and CBM33), at least one endo-xylanases (EC 3.2.1.8) and at least one β-xylosidases (EC 3.2.1.37).

Within a particularly preferred embodiment the above defined enzyme composition further contains one or more enzymes selected from β-glucanase (EC 3.2.1.-), acetylxylan esterase (EC 3.1.1.72), acetylgalactan esterase (3.1.1.6)), α-arabinopyranosidase (3.2.1.-), α-galactosidase (EC 3.2.1.22), ß-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endolyase (EC 4.2.2.23), rhamnogalacturonan lyase (EC 4.2.2.-) and β-mannosidases (EC 3.2.1.25), polygalacturonases (EC 3.2.1.15, 67, 82; GH28) and pectin/pectate lyases (EC 4.2.2.2, 6, 9, 10).

The terms "cellulases", "hemicellulases" and "pectinases" as used within the present invention of the process for the hydrolysis of biomass refer to any blend of enzymes which is involved in the hydrolytic degradation (depolymerization) of polymeric cellulose, hemicellulose and/or pectin to monomeric sugars. As used herein, the terms "cellulases", "hemicellulases" and "pectinases" refer to both naturally occurring and non-naturally occurring blends that include a plurality of enzymes as produced by an organism, for example a filamentous fungus. "Cellulases", "hemicellulases" and "pectinases" are preferably derived from fungi such as members of the subdivision *Eumycota* and *Oomycota*, including but are not limited to the following genera: *Aspergillus, Acremonium, Aureobasidium, Beauveria, Cephalosporium, Ceriporiopsis, Chaetomium, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talaromyces, Trichoderma, Thermomyces, Thermoascus, Thielavia, Tolypocladium, Trichophyton,* and *Trametes*. In a preferred implementation, the filamentous fungus is a *Trichoderma* species.

Within a preferred embodiment of the enzyme-composition the cellulases and/or pectinases are from a fungal source. Within a particularly preferred embodiment of the enzyme-composition, this fungal source is *Trichoderma reesei*.

The term "blend of enzymes" preferably refers to a blend of enzymes secreted from one single or more microbial sources. In some embodiments, enzymes for use in these blend(s) of enzymes can be prepared from one or more naturally occurring or engineered strains of filamentous fungi. Preferred strains are listed above. The desired ratio of enzyme components within the final blend(s) can be achieved by altering the relative amount of enzyme in the final blend e.g. by supplementation of purified or partially purified enzyme(s). In some embodiments, the final blend(s) may be supplemented with one or more enzyme activities that are not expressed endogenously, or expressed at relatively low level by the filamentous fungi, to improve the degradation of the cellulosic substrate to fermentable sugars. The supplemental enzyme(s) can be added as a supplement to the final blend(s) and the enzymes may be a component of a separate whole fermentation broth, or may be purified, or minimally recovered and/or purified.

As used within the process for the hydrolysis of biomass, the term "cellulase" refers to any enzyme capable of hydrolyzing cellulose polymers to shorter oligomers and/or glucose. Cellulases preferred within the enzyme composition include cellobiohydrolases (CBH) (EC 3.2.1.-), endo-1,4-β-glucanases (EG) (EC 3.2.1.4).), ß-glucosidase (EC 3.2.1.4), cellobiose hydrolase (EC 3.2.1.21), glycoside hydrolase 61 (GH61 and CBM33), expansin, swollenin, loosinin and CIP Proteins (EC 3.1.1.-; CE15).

As used within the process for the hydrolysis of biomass, the term "hemicellulase" refers to any enzyme capable of degrading or supporting the degradation of hemicellulose. Hemicellulases preferred within the enzyme composition include β-glucanases (EC 3.2.1.-), endo-xylanases (EC 3.2.1.8), β-xylosidases (EC 3.2.1.37), acetylxylan esterase (EC 3.1.1.72), acetylgalactan esterase (3.1.1.6), acetyl mannan esterase, feruloyl esterase (EC 3.1.1.73), glucuronoyl esterase (EC 3.1.1.-), α-L-arabinofuranosidase (EC 3.2.1.55), α-arabinopyranosidase (3.2.1.-), α-galactosidase (EC 3.2.1.22), ß-galactosidase (EC 3.2.1.23), α-glucuronidases (EC 3.2.1.139), β-mannase (EC 3.2.1.78), β-mannosidases (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan α-1,2-glucuronosidase (EC 3.2.1.131), endo-xylogalacturonan hydrolase (EC 3.2.1.-; GH28), α-amylase (EC 3.2.1.1), glucan 1,4-α-glucosidase (EC 3.2.1.3), galactan 1,3-galactosidase (GH43), -1,4,-endogalactanase (EC 3.5.1.89; GH53), α-rhamnosidase (EC 3.2.1.40), ß-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10), laccase (EC 1.10.3.2) and cellobiose dehydrogenase (EC 1.1.99.18).

As used within the process for the hydrolysis of biomass, the term "pectinase" refers to any enzyme capable of degrading or supporting the degradation of pectin. Pectinases preferred within the enzyme composition include polygalacturonases (EC 3.2.1.15, 67, 82; GH28), pectin/pectate lyases (EC 4.2.2.2, 6, 9, 10), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endo-lyase (EC 4.2.2.23), rhamnogalacturonan lyase (EC 4.2.2.-), rhamnogalacturonan galacturonohydrolase (EC 3.2.1.-), xylogalacturonan hydrolase (EC 3.2.1.-), pectin methylesterase (EC 3.1.1.11), beta-arabinofuranosidase (EC 3.2.1.55), beta-1,4-galactanase (EC 3.2.1.89), beta-1,3-galactanase (EC 3.2.1.90), beta-galactosidase (EC 3.2.1.23), alpha-galactosidase (EC 3.2.1.22), feruloyl acetyl esterase (EC 3.1.1.-), alpha-fucosidase (EC 3.2.1.51), (beta-fucosidase) (EC 3.2.1.38), beta-apiosidase (EC 3.2.1.-), alpha-rhamnosidase (EC 3.2.1.40), beta-rhamnosidase (EC 3.2.1.43), alpha-arabinopyranosidase (EC 3.2.1.-), beta-glucuronidase (EC 3.2.1.31), alpha-glucuronidase (EC 3.2.1.139), beta-xylosidase (EC 3.2.1.37) and alpha-xylosidase (EC 3.2.1.x).

The enzymes referenced within the present invention of the process for the hydrolysis of biomass are classified according nomenclatures that are either based on the International Union of Biochemistry and Molecular Biology's Enzyme Nomenclature and Classification (http://www.chem.qmul.ac.uk/iubmb/enzyme/) or on Carbohydrate-Active EnZYmes (http://www.cazy.org/) database.

The term "activity" of an enzyme as used within the present invention of the process for the hydrolysis of biomass refers to the catalytic activity of the enzyme under appropriate conditions under which the enzyme serves as a protein catalyst, which converts specific polymeric or artificial substrates to specific oligomeric or monomeric products. In this context the term "appropriate conditions" is well known to and applicable by a person skilled in the art.

The "contacting" according to step (a) of the inventive process may be carried out by any measure known to a person skilled in the art as suitable for the inventive purpose. It is thereby preferred that the enzyme mixture is added to the biomass while stirring the biomass within the vessel. The enzyme(s) may also be immobilized on a carrier material.

The enzymes may be employed in varied relative proportions in a given mixture. It is thereby particularly preferred to employ the enzyme composition with an E/S ratio (enzyme to substrate ratio) of from 0.05 to 1.5 wt.-%, preferably of from 0.1 to 0.75 wt.-%.

It is further preferred that the process of the present invention, particularly the step of hydrolysis, does not involve the use of acidic and/or alkaline substances, as the use of these substances will lead to the formation of compounds inhibitory to enzymes and/or microorganisms used during hydrolysis and/or fermentation. In addition, acid(s) and/or alkaline(s) will not only hydrolyze glycosidic bonds but also react with glucose and xylose molecules already present within the hydrolysate to undesired compounds such as hydroxymethylfurfural and furfural.

Further, large amounts of acids, especially of hydrochloric acid, may even prohibit the use of stainless steel equipment such as vessels, reactors and pipes and necessitate the use of a huge amount of neutralizing substances which will again increase the amount of undesirable salts within the hydrolysate.

In a preferred embodiment, step (a) of the process for the hydrolysis of biomass is carried out for a time sufficient to hydrolyze at least 20 wt.-%, preferably at least 30 wt.-%, more preferred at least 50 wt.-% and most preferred at least 60 wt.-% of the biomass. Within a further preferred embodiment of the process of the present invention, step (a) is carried out for a time sufficient to hydrolyze from 10 to 100 wt.-%, preferably from 20 to 90 wt.-% even more preferred from 30 to 85.0 wt.-% and most preferred from 40 to 75 wt.-% of the cellulose of the biomass. Within the present invention, the term "hydrolyze" is to be understood as the hydrolytic conversion of insoluble polymeric components of the biomass to soluble monomeric, dimeric and/or oligomeric compounds by chemical, physical, and/or enzymatic processes such as hydrolysis.

Within a particularly preferred embodiment, step (a) of the process for the hydrolysis of biomass is carried out for 1 minute to 112 hours, more preferred for 30 minutes to 100 hours, particularly preferred for 1 hour to 96 hours, even more preferred for 4 hours to 85 hours also particularly preferred from 12 hours to 72 hours.

Within a further preferred embodiment, step (a) of the process for the hydrolysis of biomass is carried out until the content of remaining insoluble solids is less than 40 wt.-%, preferably less than 30 wt.-%, even more preferred less than 20 wt.-% and most preferred less than 15 wt.-%. In a further preferred embodiment, step (a) of the process for the hydrolysis of biomass is carried out until the content of remaining insoluble solids is from 5 to 40 wt.-%, preferably from 8 to 30 wt.-% and most preferred from 10 to 25 wt.-%.

Within another preferred embodiment of the present invention of the process for the hydrolysis of biomass, step (a) is carried out until the biomass is liquefied to at least 50%, preferably at least 60% and most preferred at least 80%, wherein a liquefaction of from 60 to 90% is particularly preferred.

The reaction temperature during step a) is preferably selected from 25 to 80° C., more preferred selected from 30 to 75° C. and particularly preferred from 35 to 65° C. In another preferred embodiment, step (a) of the process for the hydrolysis of biomass is carried out for 1 to 80 hours, preferably 2 to 70 hours, more preferred 3 to 60 hours, wherein the temperature is selected from 35 to 75° C. or from 45 to 65° C.

Within another preferred embodiment, the pH during step a) is preferably selected from 4 to 6, particularly preferred from 4.5 to 5.5.

The appropriate dosage levels and operating conditions will be apparent to those of skill in the art, especially in light of the detailed disclosure provided herein. Optimum dosage levels of the whole fermentation broth will vary considerably depending upon the substrate and the pretreatment technologies used. The enzyme composition is preferably added to the biomass in an amount of from 0.1 to 24 wt.-% of the dry matter of the biomass, more preferred 0.25 to 12 wt.-% of the dry matter of the biomass, particularly preferred being 0.5 to 6 wt.-% of the dry matter of the biomass and most preferred from 0.1 to 0.6 wt.-% of the dry matter of the biomass. The total enzyme (protein) concentration was determined by the Bradford method with bovine serum albumin as a reference standard (Bradford, M., 1976).

Step (a) of the process for the hydrolysis of biomass is carried out within any kind of vessel known to a person skilled in the art as suitable for the inventive process, preferably within a reactor. Suitable reactors are within the knowledge of a person skilled in the art. Preferable vessels/reactors include but are not limited to vessels/reactors comprising a stirring measure and/or a measure for pumping over or recirculating the biomass content within the reactor. Further preferred measures of preferred reactors include but are not limited to measures for temperature and/or pH-controlling and regulation of temperature and/or pH.

Following step (a) of the inventive process a solid and a liquid phase are separated according to step (b) of the inventive process. The separation of the solid and the liquid phase may be carried out by any measure known to a person skilled in the art as suitable for the inventive purpose and is preferably carried out by filtration, centrifugation, decantation or pressing e.g. by a screw-press.

The temperature of the liquid phase is preferably the same as the temperature during the contacting according to step (a) of the inventive process. Within a particularly preferred embodiment, the temperature of the liquid phase is selected from 25 to 60° C., further preferred from 30 to 55° C. In case the temperature of the separated liquid phase is below the temperature during the contacting according to step (a), the liquid phase is preferably cooled down by conveying the liquid phase through a heat exchanger after separation from the solid phase according to step (b) of the inventive process.

According to step (c) of the inventive process an enzymatic conversion of the separated solid phase is carried out. It is either possible to convert the solid phase by utilization of the enzymes still present within the material. This is particularly preferred in case the enzymes added during step (a) of the process are apt to immobilization on the solid particles still present within the solid phase. It is, however, also possible to add further enzymes during step (c). In case enzymes are added, it is either possible to add the same or different enzymes compared to step (a).

Within a particularly preferred embodiment, the temperature during step (c) is preferably selected from 25 to 80° C., further preferred from 30 to 75° C. and most preferred from 35 to 65° C.

Within another preferred embodiment, the pH during step (c) is preferably selected from 4 to 6, particularly preferred from 4.5 to 5.5.

Within another preferred embodiment, step (c) is preferably carried out for at least 30 minutes, more preferred for at least 60 minutes, even more preferred for at least 90 minutes and most preferred for at least 120 minutes before combining at least part of the solid phase according to step (d) with the liquid phase. It is thereby particularly preferred that step (c) is carried out for from 1 minute to 112 hours, more preferred for 30 minutes to 100 hours, particularly preferred for 1 hour to 96 hours, even more preferred for 4 hours to 85 hours also particularly preferred from 12 hours to 72 hours.

Within a particularly preferred embodiment at least one enzyme selected from the class of hydrolases is added to the solid phase. The term "hydrolases" is thereby defined as described before. It is within the scope of the present invention to add the same or different hydrolases within step (a) and step (c).

Within a further preferred embodiment, an amount of liquid, preferably $H_2O$, is added to the solid phase before or during step (c). The amount is preferably chosen to guarantee a final dry matter content of the solid phase of from 15 to 35%, preferably from 18 to 30% and most preferred from 20 to 25%.

Regarding the enzymatic conversion according to step (c) it is further possible to choose the same or different conditions, parameters and concentrations as defined above regarding step (a) of the process. The same definitions apply accordingly.

Within a further preferred embodiment of the process of the present invention a solid-liquid separation is carried out after step (c). Thereby, only the separated liquid phase would be fed to the converted solid phase of step (d). The solid-liquid separation is preferably carried out by use of a filter press.

According to step (d) of the inventive process, at least part of the converted solid phase of step (c) is combined with the liquid phase of step (b). The term "converted solid phase" is thereby to be understood as the solid phase separated according to step (b) which has already undergone enzymatic conversion of at least 1 minute, preferably at least 30 minutes, more preferred at least 1 hour, particularly preferred at least 4 hours, also preferred at least 6 hours and most preferred at least 12 hours. It is thereby particularly preferred that the enzymatic conversion has been carried out for a time period of from 4 hours to 108 hours, preferably from 6 hours to 96 hours and most preferred of from 12 to 72 hours.

Within a particularly preferred embodiment of the process of the present invention, the "combining" according to step (d) is carried out by feeding the at least part of the converted solid phase to the liquid phase of step (b), wherein it is particularly preferred that from 10 to 100 wt.-%, preferably from 20 to 100 wt.-%, further preferred from 50 to 100 wt.-% of the "converted solid phase" are fed to the liquid phase according to step (d). It is, however, also within the scope of the present invention that the combining is carried out by feeding the liquid phase to the converted solid phase or by a concurrent combination of both phases.

It is thereby preferred to feed the converted solid phase continuously or by a single addition to the liquid phase. If the converted solid phase is fed continuously, at least 10 wt.-% of the converted solid phase is fed to the liquid phase per hour, preferably at least 20 wt.-%, more preferred at least 30 wt.-%. It is thereby also preferred that from 10 to 50 wt.-%, preferably from 15 to 45 wt.-% of the converted solid phase are fed to the liquid phase per hour. If the "converted solid phase" of step (c) is fed to step (d) in a continuous fashion, the feeding may start immediately after step (c) of the inventive process or start within a time period of from 1 second to 144 hours, preferably of from 1 minute to 122 hours, further preferred of from 1 hour to 96 hours, more preferred of from 6 hours to 72 hours and most preferred of from 12 hours to 48 hours. It is particularly preferred to feed from 15 to 45 wt.-% of the converted solid phase per hour and start the feeding after 12 to 48 hours after step (c).

The feeding is thereby carried out by any measure known to a person skilled in the art as suitable for the inventive process such as pumping a part of said biomass through a pipeline.

The term "reaction volume" thereby relates to the total volume of biomass and enzyme composition present in the vessel.

Within a particularly preferred embodiment, the feeding according to step (d) is preferably carried out by implementation of a heat exchanger. By implementing a heat exchanger it is not only possible to regain and recycle heat energy from the enzymatic conversion process but the so-treated material will also be cooled down to a temperature more favorable for optional subsequent fermentation. The term "heat exchanger" is well known to a person skilled in the art and comprises any device known to a person skilled in the art as suitable for the inventive purpose.

Within a preferred embodiment of the process for the hydrolysis of biomass, steps (a) to (d) are repeated at least once to ensure the at most possible yield of the desirable compounds of the biomass. Within a particularly preferred embodiment, steps (a) to (d) are repeated from 2 to 100000 times, preferably from 10 to 70000 times, more preferred from 15 to 50000 times and most preferred from 17 to 10000 times. It is within the scope of the present invention that a cleaning step of a vessel and/or any other part of the system is carried out at any time in between or after steps (a) to (d). The cleaning may be carried out by any measure known to a person skilled in the art as suitable for the inventive purpose and may also include exchange of one or more parts of the system.

Within a further particularly preferred process the steps (a) to (d) are at least partially carried out simultaneously and/or continuously.

In a particularly preferred embodiment of the inventive process, the enzyme composition added to the biomass is added in an amount of from 0.1 to 3 wt.-% of dry matter of the biomass and the process step (b) is started after 5 to 100 hours. In another particularly preferred embodiment of the process the enzyme composition added to the biomass is in an amount of from 0.25 to 2 wt.-% of dry matter of the biomass and the process step (b) is started after 10 to 72 hours.

Within a preferred embodiment at least one fermentation organism is added to the liquid phase before, during or after step (d) of the process, whereas within a particularly preferred embodiment the fermentation organism is added to the liquid phase before or during step (d) of the process.

According to a particularly preferred embodiment, the temperature during the addition of the at least one fermentation organism is selected from 10 to 65° C., preferably from 15 to 55° C., especially preferred from 20 to 50° C., most preferred from 25 to 45° C.

The fermentation organism is particularly preferred a mesophilic yeasts such as all species of genus *Saccharomyces*, especially *Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum, Saccharomyces zonatus*, as well as *Arxula adeninovorans, Ashbya gossypii, Hansenula polymorpha, Debaramyces hansenii, Hortea werneckii, Kluyeveromyces lactis, Schwanniomyces occidentalis, Thrichosporon domesticum, Thrichosporon montevideense, Xanthophyllomyces dendrohous, Yarowia lypolytica, Zygosaccharomyces bailii, Zygosaccharomyces rouxii, Schizosaccharomyces pombe, Pichia stipitis, Pichia segobiensis, Candida shehatae, Candida tropicalis, Candida boidinii, Candida tenuis, Pachysolen tannophilus, Hansenula polymorpha, Candida famata, Candida parapsilosis, Candida rugosa, Candida sonorensis, Candida maltosa, Issatchenkia terricola, Kloeckera apis, Pichia barkeri, Pichia cactophila, Pichia deserticola, Pichia norvegensis, Pichia membranefaciens, Pichia mexicana* and *Torulaspora delbrueckii, Rhodosporidium toruloides, Rhodotorula glutinis, Lipomyces starkeyi, Lipomyces lipofer, Cryptococcus albidus* and mixtures thereof.

In an alternative embodiment of the inventive process, the at least one fermentation organism is selected from thermophilic micro-organisms. Examples of thermophilic yeasts suitable for the inventive process are *Candida bovina, Candida picachoensis, Candida emberorum, Candida pintolopesii, Candida thermophila, Kluyveromyces marxianus, Kluyveromyces fragilis, Kazachstania telluris, Issatchenkia orientalis* and *Lachancea thermotolerans*. Preferred thermophylic bacteria include *Clostridium thermocellum, Clostridium thermohydrosulphuricum, Clostridium thermosaccharolyticum, Thermoanaerobium brockii, Thermobacteroides acetoethylicus, Thermoanaerobacter ethanolicus, Clostridium thermoaceticum, Clostridium thermoautotrophicum, Acetogenium kivui, Desulfotomaculum nigrificans* and *Desulvovibrio thermophilus, Thermoanaerobacter tengcongensis, Bacillus stearothermophilus* and *Thermoanaerobacter mathranii*.

The use of the following mesophilic yeasts is especially preferred: *Saccharomyces cerevisiae, Pichia stipitis, Pachysolen tannophilus, Candida shehatae*.

In an alternative embodiment of the inventive process, the at least one fermentation organism is selected from fungi. Examples of fungi suitable for the inventive process are *Aspergillus* sp., *Trichoderma* sp., *Penicillium* sp., *Acremonium* sp., *Rhizopus* sp. and *Talaromyces* sp.

In an alternative embodiment of the inventive process, the at least one fermentation organism is selected from bacteria. Examples of bacteria suitable for the inventive process are *Clostridium acetobutylicum, Lactobacillus brevis, Lactobacillus bulgaricus, Lactobacillus casei, Lactobacillus helveticus, Lactobacillus lactis, Lactococcus lactis, Leuconostoc mesenteroides, Lactobacillus* sp., *Zymomonas mobilis, Escherichia coli, Bacillus subtilis, Bacillus licheniformis*.

Within a preferred embodiment, minerals such as copper, zinc, magnesium, calcium, iron and nitrogen-containing compounds such as nitrate, amino acids, ammonia are added before, during or after addition of the at least one fermentation organism.

Valuable organic compounds resulting from bacterial fermentation of the hydrolysate comprise but are not limited to organic acids (such as acetic acid, lactic acid, succinic acid, itaconic acid, fumaric acid, propionic acid, and glucuronic acid), amino acids (such as glutamic acid, leucine, lysine, threonine, aspartic acid, phenylalanine, cysteine), caprolactams (such as alpha-amino-caprolactam), antibiotics (such as bleomycin, virginiamycin, lincomycin, monensin, blasticidin, tetracycline), vitamins (such as vitamin B2, B12 and C), enzymes, nucleotides/nucleosides (such as NADH, ATP, cAMP, FAD, coenzyme A), biogas, biopolymers (such as polyhydroxybutyrate, polyamides/fibroins), proteins, polysaccharides (such as xanthan, dextran), amino glucans (such as hyaluronic acid) as well as organic solvents and biofuels (such as acetone, ethanol, butanol, propanediol).

Valuable organic compounds resulting from yeast fermentation of the hydrolysate comprise but are not limited to organic solvents (e.g. ethanol, propanol), nucleotides (e.g. RNA), biosurfactants (e.g. sophorose lipids), enzymes, and biopolymers (e.g. spidroins).

Valuable organic compounds resulting from fungal fermentation of the hydrolysate comprise organic acids (such as citric acid, fumaric acid, itaconic acid), antibiotics (such as penicillin, cephalosporin), enzymes, and polysaccharides (such as chitin).

In a further preferred embodiment of this process the organic compound is selected from alcohols, organic acids, biopolymers, antibiotics, amino acids, caprolactams, polysaccharides, organic solvents, biofuels, aminoglucans, nucleotides/nucleosides, vitamins, biosurfactants, enzymes and mixtures thereof.

It is a major advantage of the process of the present invention that the process may be carried out as a continuous process whereas—particularly preferred—at least two process cycles [cycle v1n1, cycle v2n1] are started in parallel or with a gap. The variable "v" is thereby indicating the individual cycle, the variable "n" is indicating the repetition of the cycle. For example, a process according to the invention involving three cycles and running for 100 repetitions (each cycle) would be defined by using variables from v1n1, v2n1, v3n1 to v1n100, v2n100 and v3n100, wherein e.g. the $35^{th}$ repetition of the second cycle would be indicated by v2n35.

The cycles are particularly preferred started with a gap of at least 15 minutes, preferably at least 60 minutes, further preferred at least 6 hours, particularly preferred at least 12 hours, also preferred at least 24 hours and most preferred at least 48 hours, wherein a gap of from 1 hour to 96 hours, preferably of from 5 hours to 72 hours, also preferred of from 6 hours to 48 hours or from 10 hours to 24 hours are particularly preferred. Therefore, each subsequent process cycle [v2, v3, etc.] is using enzymatically converted solid phase from the previous phase [starting from v1] as shown within FIG. 1. In case the inventive process is carried out in 2 cycles, the cycles are preferably started with a gap of from 24 to 72 hours, preferably of from 36 to 48 hours, in case the inventive process is carried out in 4 cycles, the cycles are preferably started with a gap of from 12 to 72 hours, preferably of from 18 to 24 hours.

If the process for the hydrolysis of biomass according to the present invention is carried out within more than one cycle, it is particularly advantageous if steps (a) and (c) are carried out concurrently for at least 50% of the time period of step (a), preferably from 50 to 95%, particularly preferred from 60 to 90% and most preferred from 70 to 85%. It is equally preferred that steps (a) and (c) are carried out concurrently for 100% of the time period.

If the process for the hydrolysis of biomass according to the present invention is carried out within more than one cycle, it is particularly advantageous if steps (a) and (d) are carried out concurrently for at least 50% of the time period of step (a), preferably from 50 to 95%, particularly preferred from 60 to 90% and most preferred from 70 to 85%.

It is equally preferred that steps (a) and (d) are carried out concurrently for 100% of the time period.

It is thereby possible to carry out each cycle under the same or different conditions such as but not limited to the dry matter content of the biomass, enzyme composition used, the temperature of the individual steps etc.

In the following particularly preferred embodiments of the process are described which are not to be understood as limiting the invention in any respect.

Particularly Preferred Embodiment 1

Particularly preferred is a process for the hydrolysis of sugar cane straw and/or bagasse comprising the steps of
a) Contacting the biomass with an enzyme-composition containing at least one cellobiohydrolase (EC 3.2.1.-) and at least one endo-,4-β-glucanase (EC 3.2.1.4) in a vessel for a time period of from 4 hours to 85 hours also particularly preferred from 12 hours to 72 hours;
b) Separating a solid and a liquid phase;
c) Enzymatic conversion of the solid phase for a time period of from 4 hours to 85 hours also particularly preferred from 12 hours to 72 hours;
d) Feeding of at least part of the converted solid phase of step (c) to the liquid phase of step (b)
wherein at least one enzyme selected from cellobiohydrolase (EC 3.2.1.-) and at least one endo-,4-β-glucanase (EC 3.2.1.4) is added during step (c) and wherein the feeding according step (d) is carried out continuously with a feeding rate of from 10 to 20 wt.-% per hour.

Particularly Preferred Embodiment 2

Particularly preferred is a process for the hydrolysis of sugar cane straw and/or bagasse comprising the steps of
a) Contacting the biomass with an enzyme-composition containing at least one cellobiohydrolase (EC 3.2.1.-), at least one endo-,4-β-glucanase (EC 3.2.1.4), at least one ß-glucosidase (EC 3.2.1.4), at least one glycoside hydrolase 61 (GH61 and CBM33), at least one endo-xylanases (EC 3.2.1.8) and at least one β-xylosidases (EC 3.2.1.37) in a vessel for a time period of from 4 hours to 85 hours also particularly preferred from 12 hours to 72 hours;
b) Separating a solid and a liquid phase;
c) Enzymatic conversion of the solid phase for a time period of from 4 hours to 85 hours also particularly preferred from 12 hours to 72 hours;
d) Feeding of at least part of the converted solid phase of step (c) to the liquid phase of step (b)
wherein at least one enzyme of the enzyme composition as defined within step (a) above is added during step (c) and wherein the feeding according step (d) is carried out continuously with a feeding rate of from 10 to 20 wt.-% per hour.

Particularly Preferred Embodiment 3

Particularly preferred is a process for the hydrolysis of sugar cane straw and/or bagasse as defined above regarding particularly preferred embodiment 2, wherein the above defined enzyme composition further contains one or more enzymes selected from β-glucanase (EC 3.2.1.-), acetylxylan esterase (EC 3.1.1.72), acetylgalactan esterase (3.1.1.6)), α-arabinopyranosidase (3.2.1.-), α-galactosidase (EC 3.2.1.22), ß-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endolyase (EC 4.2.2.23), rhamnogalacturonan lyase (EC 4.2.2.-) and β-mannosidases (EC 3.2.1.25), polygalacturonases (EC 3.2.1.15, 67, 82; GH28) and pectin/pectate lyases (EC 4.2.2.2, 6, 9, 10).

Particularly Preferred Embodiment 4

Particularly preferred is a process for the hydrolysis of sugar cane straw and/or bagasse as defined above regarding any of particularly preferred embodiments 1 to 3, wherein step d) is carried out by combining the converted solid phase of step (c) to the liquid phase of step (b) within one batch.

Particularly Preferred Embodiment 5

Particularly preferred is a process for the hydrolysis of sugar cane straw and/or bagasse as defined above regarding any of particularly preferred embodiments 1 to 4 running from 2 to 4 cycles (v1, v2, v3, v4) for from 10 to 100 repetitions (n1 to n100) wherein step a) and/or c) is/are carried out at 45 to 55° C., pH 4.5 to 5.5, for 72 to 108 hours at a rpm of from 40 to 60. The enzyme composition is preferably added with an E/S (enzyme to substrate ratio) of from 0.1 to 0.75%.

It is thereby particularly preferred to start each cycle with a gap of from 36 to 72 hours. It is further particularly preferred to implement a heat exchanger between steps c) and d) to cool down the combined post-saccharified solid phase and the pre-saccharified biomass to a suitable fermentation temperature from 25 to 40° C. The fermentation is particularly preferred carried out at a pH from 4.5 to 5.5, at a rpm of from 150 to 250 for a time period of from 12 to 72 hours wherein the fermenting organism is preferably added in an amount of from 7.5 to 12.5% (wt./wt.) seed culture.

Particularly Preferred Embodiment 6

Particularly preferred is a process for the hydrolysis of sugar cane straw and/or bagasse as defined above regarding any of particularly preferred embodiments 1 to 5, wherein the enzyme composition is added in form of a blend produced by an organism, for example a filamentous fungus. The fungus is preferably a species from the genus *Trichoderma*, particularly preferred *Trichoderma reesei*. It is thereby preferred to further add one or more enzymes selected from β-glucanase (EC 3.2.1.-), acetylxylan esterase (EC 3.1.1.72), acetylgalactan esterase (3.1.1.6)), α-arabinopyranosidase (3.2.1.-), α-galactosidase (EC 3.2.1.22), ß-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.-), rhamnogalacturonase (EC 3.2.1.-; GH28), rhamnogalacturonan acetylesterase (EC 3.1.1.86), rhamnogalacturonan endolyase (EC 4.2.2.23), rhamnogalacturonan lyase (EC 4.2.2.-) and β-mannosidases (EC 3.2.1.25), polygalacturonases (EC 3.2.1.15, 67, 82; GH28) and pectin/pectate lyases (EC 4.2.2.2, 6, 9, 10), cellobiohydrolase (EC 3.2.1.-), endo-,4-β-glucanase (EC 3.2.1.4), ß-glucosidase (EC 3.2.1.4), glycoside hydrolase 61 (GH61 and CBM33), endo-xylanases (EC 3.2.1.8), β-xylosidases (EC 3.2.1.37), cellobiohydrolase (EC 3.2.1.-) and endo-,4-β-glucanase (EC 3.2.1.4).

FIGURES

The present invention is now described by the following example and figures. The example and figures are for illustrative purposes only and are not to be understood as limiting the invention.

FIG. 3 shows the time scale of an equipment occupation plan implementing a process with 4 cycles and 50 repetitions

EXAMPLES

Example 1

Figure 1:
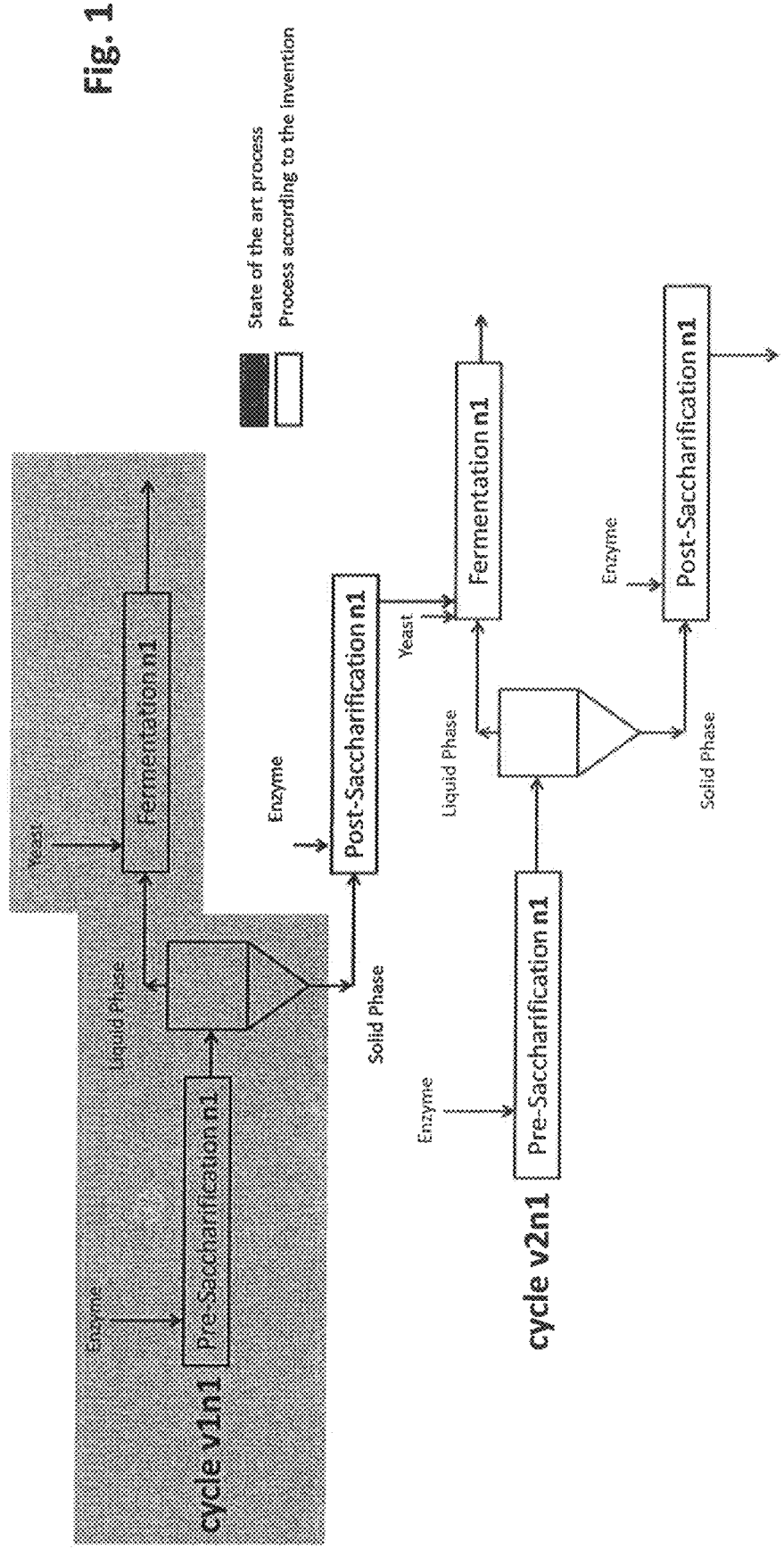
FIG. 1 shows a flow chart depicting the inventive process as carried out within the example 1

Continuous process of two parallel cycles [cycle v1, cycle v2] using pretreated sugar cane bagasse biomass in combination with the addition of fermenting organisms. The schematic is shown in FIG. 1.

The contacting of the steam-pretreated sugar cane bagasse biomass according to step (a) [cycle v1] was carried out in a stirred tank reactor system with a temperature and a pH control device ("Pre Saccharification" cycle v1n1) at a dry matter content of 20 wt.-%. An enzyme composition containing 91.3 wt.-% Celluclast® (Cellulase from *Trichoderma reesei* ATCC 26921, C2730 Sigma) and 8.7 wt.-% Glucosidase (49291 Sigma) with an enzyme to solid ratio of 0.5 wt.-% was added to the biomass. Enzymatic conversion was carried out at 50° C., pH 5.0 for 48 hours with stirring at 50 rpm. After step (a), a solid-liquid separation was performed with a decanter centrifuge to recover the sugar containing liquid phase [cycle v1n1].

After 48 hours a parallel batch [cycle v2] was started for additional 48 h under the same conditions as described for [cycle v1] ("Pre Saccharification" cycle v2n1).

The solid phase obtained within [cycle v1n1] contained lignin and the remaining cellulose and was subjected to further enzymatic conversion according to step (c) [cycle v1n1] ("Post Saccharification" cycle v1n1). The further enzymatic conversion was also carried out in a stirred tank reactor system with a temperature and pH control device. After adding an enzyme composition as defined before regarding step (a) with an enzyme to solid ratio of 0.5%, and water to achieve a solid content of 20% (wt/wt), the enzymatic conversion was performed for additional 48 h at 50° C., pH 5.0 and 50 rpm. After the conversion, the converted solid phase was transferred over a heat-exchanging-device (wherein the temperature was cooled down to 32° C.) to the liquid phase of the parallel batch [cycle v2n1].

A fermenting organism was added to the liquid phase [cycle v2n1] and converted solid phase [cycle v1n1] in a stirred tank bioreactor system with a temperature and pH control device (=cultivation vessel) ("Fermentation"). Therefore, a 10% (wt./wt.) seed culture of a *Saccharomyces cerevisiae* yeast strain (DSM No.: 1333) was added. Conditions were chosen 32° C. and pH 5.0 in anaerobic conditions at 200 rpm for 64 hours.

The solid phase [cycle v2n1] was treated under the same conditions as described for [cycle v1n1] ("Post Saccharification" cycle v2n1).

Figure 2:
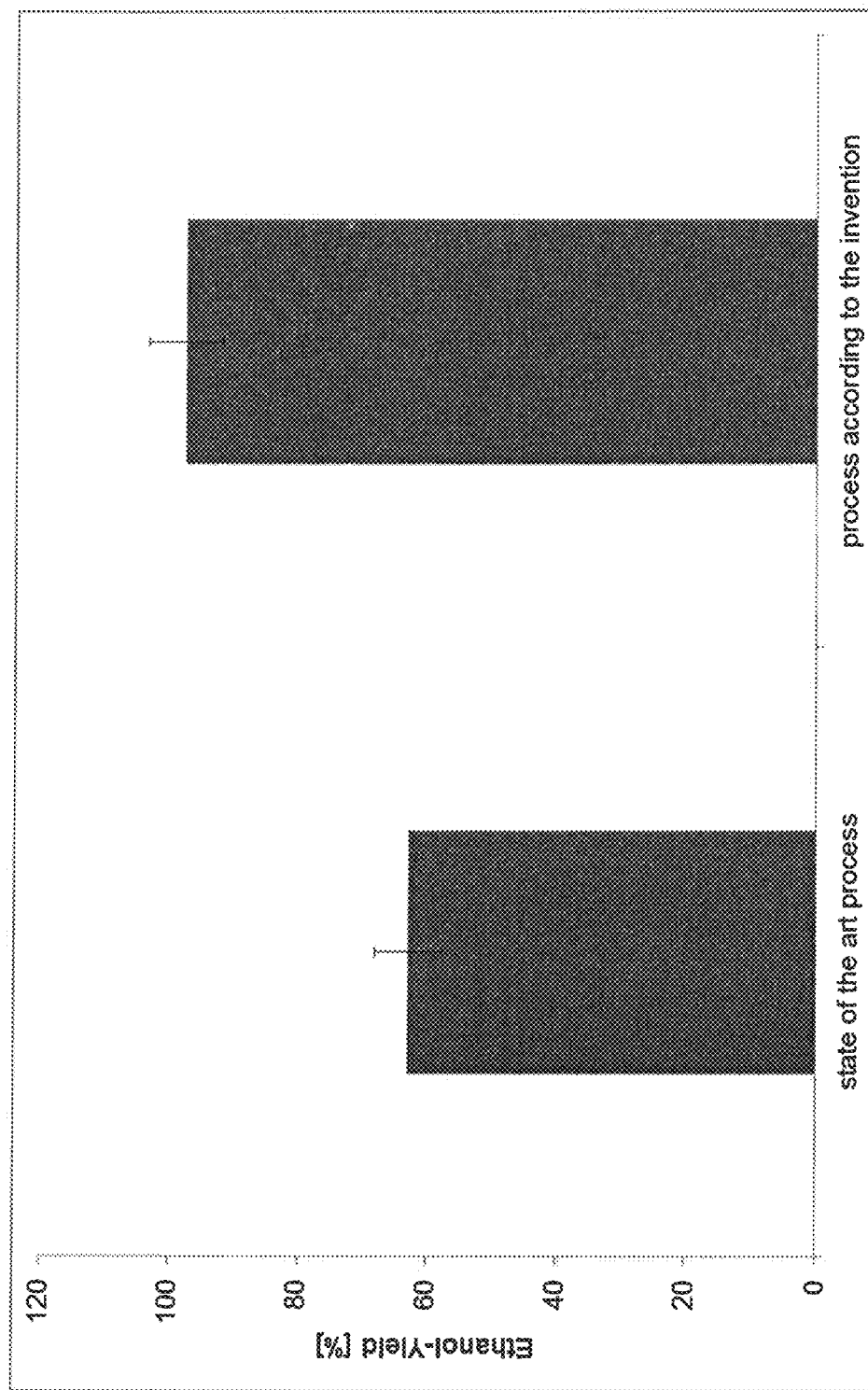
FIG. 2 shows a comparison of the yields of glucose of a convention process and the process according to the present invention

It could be proven by the example that the inventive process leads to a 97.7% hydrolysation/saccharification of the pretreated sugar cane bagasse biomass and may be implied within parallel running processes to guarantee an efficient and continuous conversion. The results are shown in FIG. 2. It can be seen from FIG. 2 that the ethanol yield was significantly improved compared to a standard process according to the state of the art (no solid-phase post saccharification according to step c) but otherwise identical process conditions).

It could also be proven that the inventive process concept is suitable for a partially parallel and continuous conduction.

Example 2

Industrial scale continuous process of four parallel cycles [cycle v1, cycle v2, cycle v3, cycle v4] running 49 repetitions using pretreated sugar cane bagasse biomass in combination with the addition of fermenting organisms. The schematic is shown in FIG. 3. The process conditions have been chosen as defined before regarding example 2 if not stated otherwise hereunder.

Each cycle was carried out by use of 3 different vessels (pre-saccharification vessel v1pre, postsaccharification vessel v1post, fermentation vessel v1fer)
Timescale per process step:
Pre-Saccharification (step (a) and Post-Saccharification (step (c)) are divided into the following sub-process steps:
 Filling of the reaction vessel: 6 h
 Reaction: 48 h
 Emptying of the reaction vessel: 6 h
 CIP (cleaning in place) of the reaction vessel: 4 h
Fermentation (included into process step (d)):
 Filling of the reaction vessel: 14 h
 Reaction: 48 h
 Emptying of the reaction vessel: 6 h
 CIP of the reaction vessel: 4 h

What is claimed is:

1. A process for the hydrolysis of biomass comprising the steps of:
   a) Contacting the biomass with an enzyme-composition containing at least one enzyme selected from the class of hydrolases sufficient to hydrolyze at least part of the biomass to fermentable sugars in a vessel for 3 to 60 h and at a temperature of from 45 to 65° C., whereby a solid phase and a liquid phase comprising the fermentable sugars are formed;
   b) Separating the solid and liquid phases;
   c) Enzymatically converting the separated solid phase with further addition of an enzyme-composition containing at least one enzyme selected from the class of hydrolases sufficient to hydrolyze the solid phase to more fermentable sugars to produce a converted solid phase comprising more fermentable sugars:
   d) Combining at least part of the converted solid phase of step (c) with the liquid phase of step (b); wherein at least one fermentation organism is added to the liquid phase before or during step (d), wherein the temperature during the addition of the at least one fermentation organism is from 25 to 45° C., and wherein from 10 to 100 wt-% of the converted solid phase is fed to the liquid phase of step (b).

2. The process of claim 1, wherein an amount of liquid is added to the solid phase before or during step (c).

3. The process of claim 1, wherein at least one fermentation organism is added to the liquid phase after step (d) of the process.

4. The process of claim 1, wherein step (c) is carried out for at least 30 minutes before feeding at least part of the converted solid phase in step (d).

5. The process of claim 1, wherein the combining in step (d) is carried out using a heat exchanger.

6. The process of claim 1, wherein steps (a) to (d) are at least partially carried out simultaneously and/or continuously.

7. The process of claim 1, wherein the enzyme-composition in step (a) or contains at least one cellobiohydrolase (EC 3.2.1-) and at least one endo-,4-β-glucanase (EC 3.2.1.4).

8. The process of claim 1, wherein the biomass is selected from sugar-beet, sugar cane, sugar-cane straw, sugar-beet pulp, sugar-cane bagasse, straw, corn, wood, oilseed and mixtures thereof.

9. The process of claim 1, wherein the dry matter content of the biomass is in the range from 5 to 30 wt.-%.

* * * * *